United States Patent
Neela et al.

(10) Patent No.: US 11,345,683 B2
(45) Date of Patent: May 31, 2022

(54) PROCESS FOR THE PREPARATION OF LIFITEGRAST

(71) Applicant: AUROBINDO PHARMA LIMITED, Hitech (IN)

(72) Inventors: Praveen Kumar Neela, Hyderabad (IN); Guruswamy Batthini, Hyderabad (IN); Vijay Kumar Gupta Gangisetty, Hyderabad (IN); Ravikanth Dupud, Hyderabad (IN); Srikanth Sai Alur, Hyderabad (IN); Sivakumaran Meenakshisunderam, Hyderabad (IN)

(73) Assignee: Aurobindo Pharma Ltd, Hyderabad (IN)

( * ) Notice: Subject to any disclaimer, the term of this patent is extended or adjusted under 35 U.S.C. 154(b) by 0 days.

(21) Appl. No.: 17/043,657

(22) PCT Filed: Apr. 1, 2019

(86) PCT No.: PCT/IB2019/052661
§ 371 (c)(1),
(2) Date: Sep. 30, 2020

(87) PCT Pub. No.: WO2019/186520
PCT Pub. Date: Oct. 3, 2019

(65) Prior Publication Data
US 2021/0032226 A1 Feb. 4, 2021

(30) Foreign Application Priority Data

Mar. 31, 2018 (IN) .............................. 201841012294

(51) Int. Cl.
*C07D 405/06* (2006.01)
*C07C 211/27* (2006.01)

(52) U.S. Cl.
CPC .......... *C07D 405/06* (2013.01); *C07C 211/27* (2013.01)

(58) Field of Classification Search
CPC .. C07B 2200/13; C07D 405/06; C07C 211/27
USPC ....................................................... 546/148
See application file for complete search history.

(56) References Cited

FOREIGN PATENT DOCUMENTS

WO   WO-2019026014 A1 * 2/2019 ........... C07D 405/06

* cited by examiner

*Primary Examiner* — Kristin A Vajda
(74) *Attorney, Agent, or Firm* — Jay Akhave; Patent Science LLC

(57) ABSTRACT

The present invention provides dibenzylamine salt of Lifitegrast (XV), and diphenylamine salt of Lifitegrast (XVI) and the use of the above salts in the purification process of Lifitegrast (I). The present invention relates to a process for the preparation of Lifitegrast (I).

5 Claims, 1 Drawing Sheet

Fig. 1
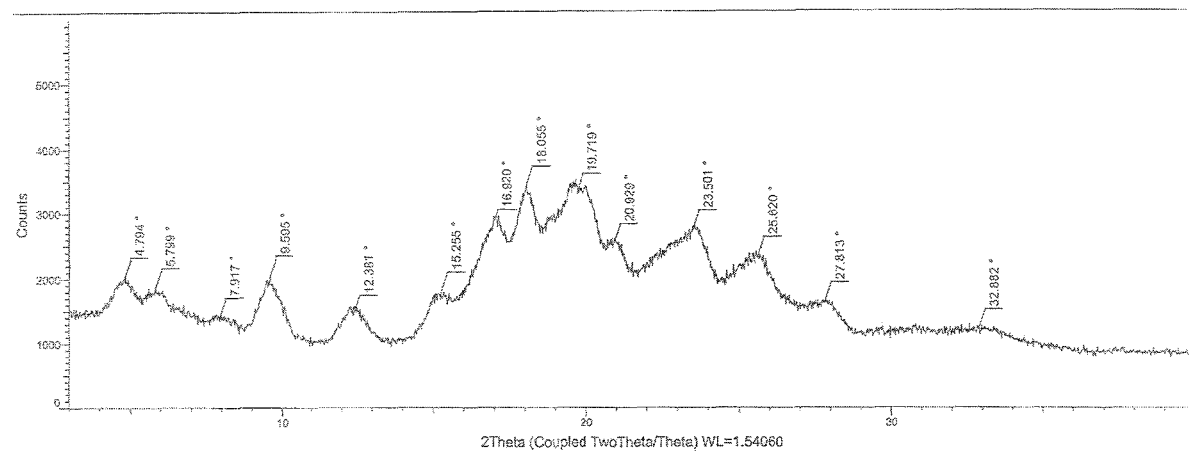
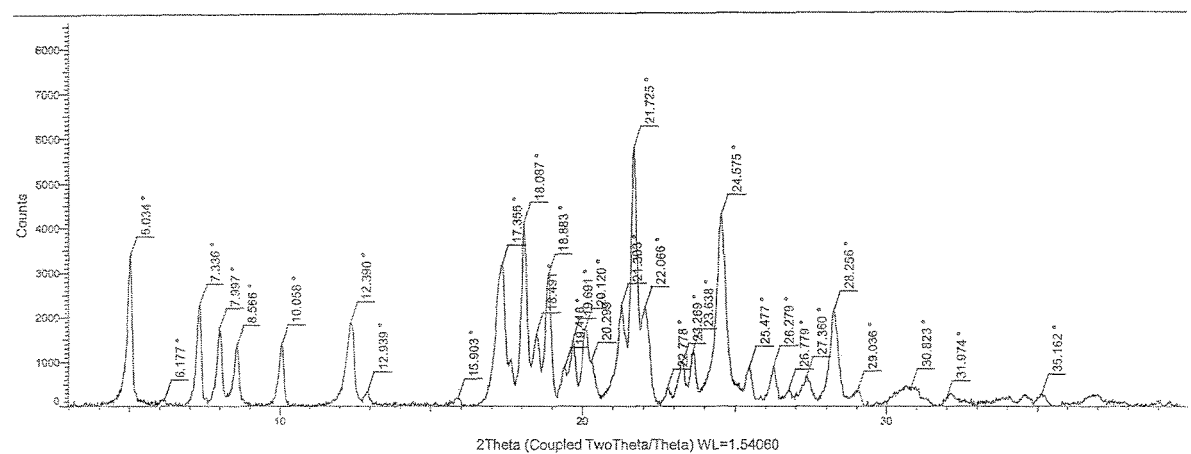
Fig. 2

PROCESS FOR THE PREPARATION OF LIFITEGRAST

FIELD OF INVENTION

The present invention relates to a process for the preparation of Lifitegrast (I).

BACKGROUND OF THE INVENTION

Lifitegrast (I) is chemically known as (S)-2-(2-(Benzofuran-6-carbonyl)-5,7-dichloro-1,2,3,4-tetrahydroisoquinoline-6-carboxamido)-3-(3-(methylsulfonyl) phenyl)propanoic acid. Lifitegrast (I) is an Ocular anti-inflammatory to treat dry eye disease. Lifitegrast (I) is being marketed in the US under the brand name Xiidra®.

Lifitegrast is disclosed in U.S. Pat. Nos. 7,314,938 and 8,084,047.

U.S. Pat. No. 8,367,701 discloses a process for the preparation of Lifitegrast (I), by reacting benzofuran carboxylic acid (II) with compound (III) to produce Lifitegrast benzyl ester (IV), which undergoes reduction using Pd/C in presence of source of protons selected from formic acid to produce Lifitegrast (I).

The process is as shown in scheme-I below:

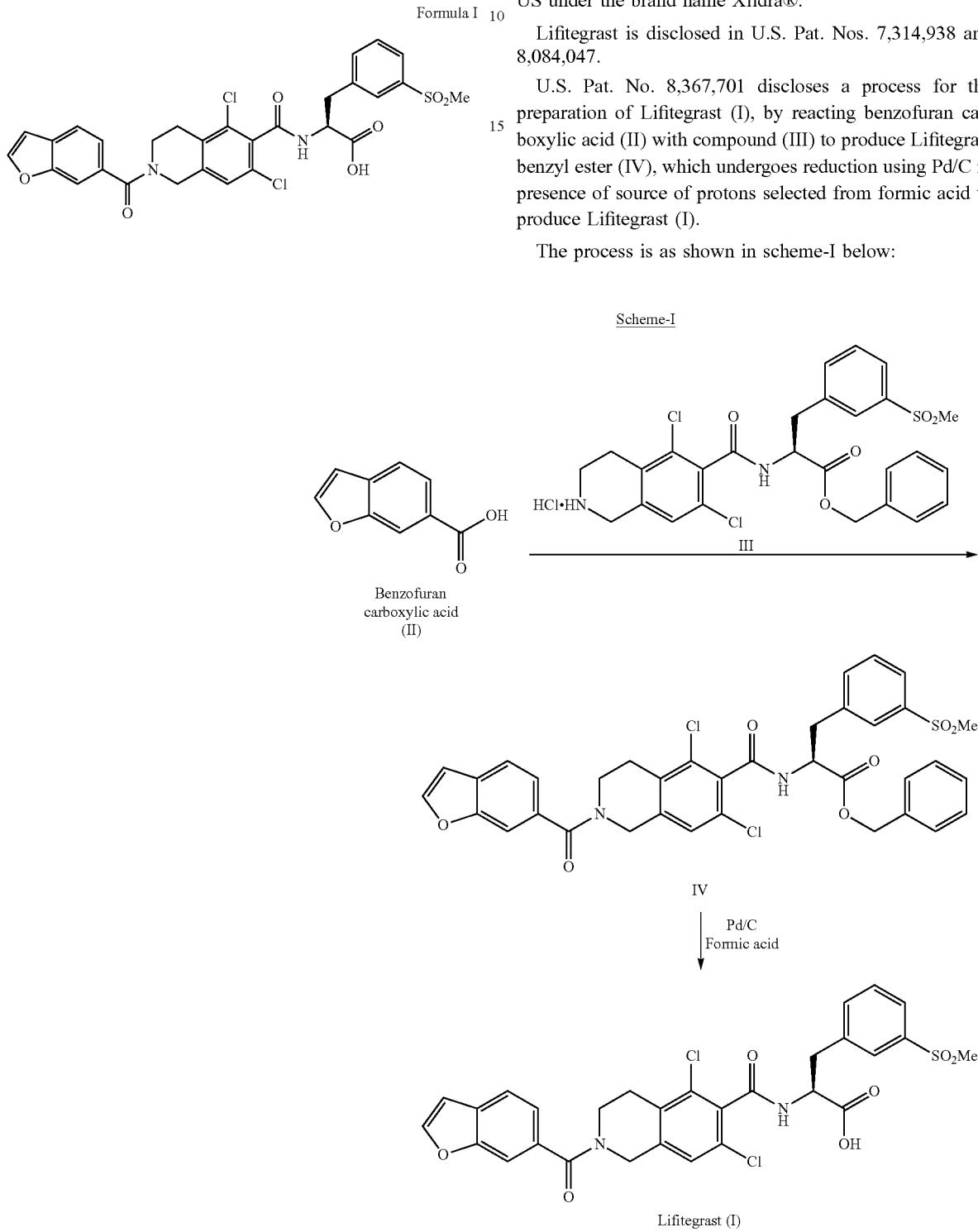

The disadvantage of the above process is de-benzylation step, which is carried out in final stage using formic acid and palladium catalyst where de-chlorination will also takes place and results the des-chloro impurities along with other unknown impurities. The removal of these impurities are difficult and required repeated purification of Lifitegrast, which results lower yield.

U.S. Pat. No. 8,927,574 discloses a process for the hydrolysis of Lifitegrast ester by performing base hydrolysis with a base in an aprotic solvent, or performing acid hydrolysis with an acid in an aprotic solvent.

The disadvantage of the above process i.e. hydrolysis at room temperature results formation of other impurities and undergoes racemization, which leads to formation of other isomer. Repeated purifications required to remove the other isomer and impurities which impact on commercial viability of the process.

U.S. Pat. No. 9,085,553 also discloses a process for the preparation of Lifitegrast, wherein Compound (V) is reacted with compound (VI) to produce compound (VII), which is converted to Lifitegrast ester protected compound (VIII), followed by hydrolysis using a base under biphasic conditions.

The process is as shown in scheme-II below:

industrially viable. Hence, there is a need to develop cost effective and commercially viable process for the preparation of Lifitegrast (I).

The present invention is directed towards a novel process for the preparation of Lifitegrast (I). The advantage of the present invention is purification of Lifitegrast (I) via dibenzylamine salt and/or diphenylamine salt.

OBJECTIVE OF INVENTION

The main objective of the present invention is to provide a simple, industrially feasible and cost effective purification process for the preparation of Lifitegrast (I) with high purity and good yield on commercial scale.

SUMMARY OF THE INVENTION

An embodiment of the present invention related to dibenzylamine salt of Lifitegrast (XV).

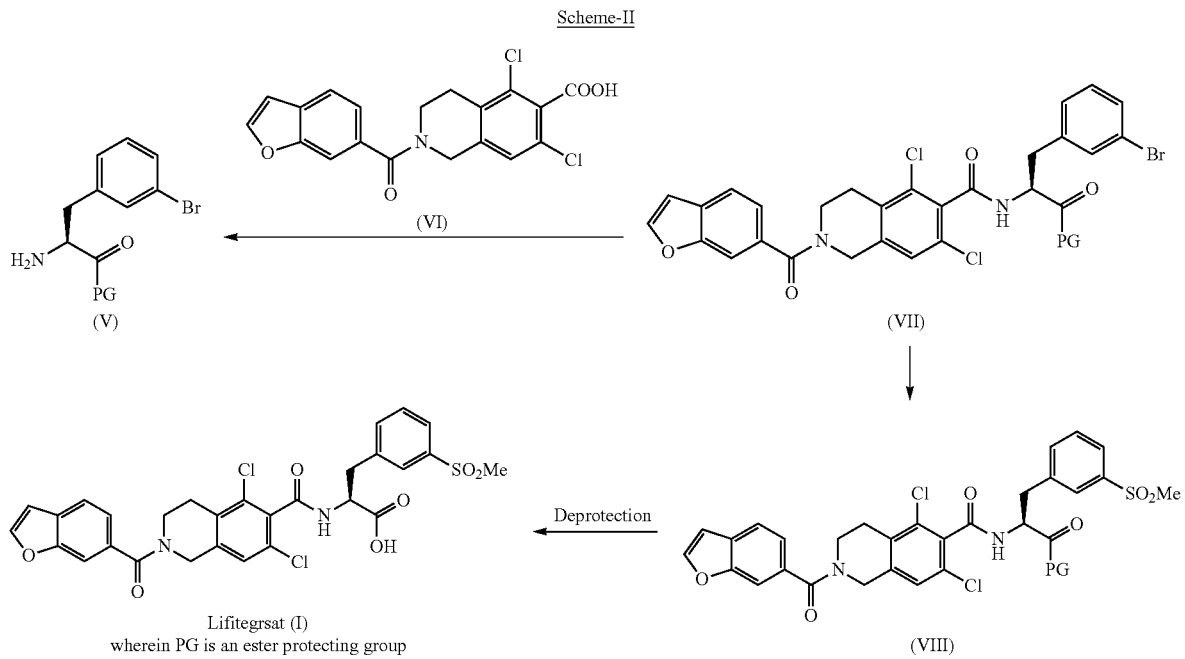

The disadvantage of the above process i.e. hydrolysis at room temperature results in the formation of other impurities and undergoes racemization which leads to formation of other isomer. Repeated purifications are required to remove the other isomer and impurities which impact on commercial viability of the process.

However, there is always a need for an alternate process, which for example, involves use of reagents that are less expensive and/or easier to handle, consume smaller amounts of reagents, provide higher yield of product, have smaller and/or more eco-friendly waste products, and/or provide a product with higher purity.

The present invention involves less reaction time; results high yield of the product, thus the process is economical and

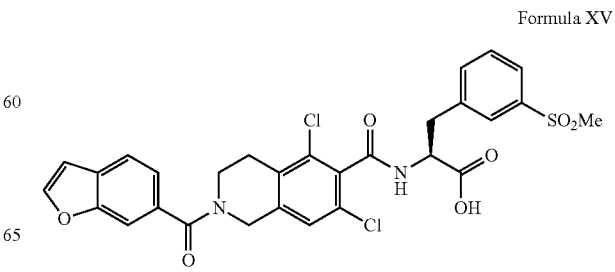

Formula XV

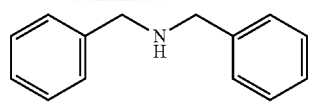

Another embodiment of the present invention provides dibenzylamine salt of Lifitegrast (XV), which is characterized by XRD having 2θ peaks at 4.79, 5.79, 7.91, 9.59, 12.38, 15.25, 16.92, 18.05, 19.71, 20.92, 23.50, 25.62, 27.81 and 32.88±0.2 2θ.

Another embodiment of the present invention is to provide a process for the purification of Lifitegrast (I), which comprises:
(i) treating Lifitegrast with dibenzylamine to get Lifitegrast dibenzylamine salt (XV);
(ii) optionally, isolating Lifitegrast dibenzylamine salt (XV);
(iii) treating the Lifitegrast dibenzylamine salt (XV) with an acid;
(iv) isolating pure Lifitegrast (I).

Other embodiment of the present invention related to diphenylamine salt of Lifitegrast (XVI).

Formula XVI

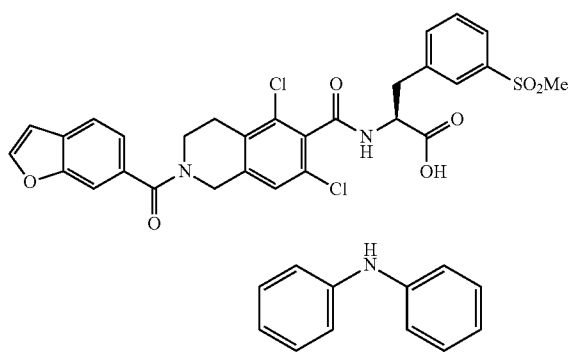

Yet another embodiment of the present invention provides diphenylamine salt of Lifitegrast (XVI), which is characterized by XRD having 2θ peaks at 5.03, 6.17, 7.33, 7.99, 8.56, 10.05, 12.39, 12.93, 15.90, 17.35, 18.08, 18.49, 18.88, 19.41, 19.69, 20.12, 20.29, 21.30, 21.72, 22.06, 22.77, 23.26, 23.63, 24.57, 25.47, 26.27, 26.77, 27.36, 28.25, 29.03, 30.82, 31.97 and 35.16±0.2 2θ.

Another embodiment of the present invention is to provide a process for the purification of Lifitegrast (I), which comprises:
(i) treating Lifitegrast with diphenylamine to get Lifitegrast diphenylamine salt (XVI);
(ii) optionally, isolating Lifitegrast diphenylamine salt (XVI);
(iii) treating the Lifitegrast diphenylamine salt (XVI) with an acid;
(iv) isolating pure Lifitegrast (I).

Still another embodiment of the present invention is to provide a process for the preparation of compound (XIV) or salt thereof.

Formula XIV

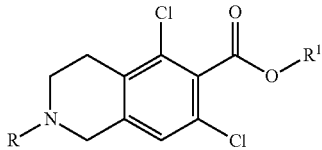

wherein, R is hydrogen or a N-protecting group and $R^1$ is $C_1$-$C_3$ alkyl group; which comprises, reacting a compound (IX) or salt thereof, Formula IX

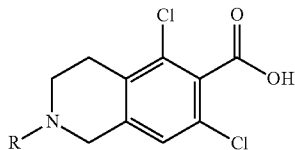

wherein, R is as defined above,
with alkyl halide to obtain a compound (XIV) or salt thereof.

Still another embodiment of the present invention is the use of compound (XIV) or salt thereof in the preparation of Lifitegrast (I).

Yet another embodiment of the present invention is to provide a process for the preparation of Lifitegrast (I), Formula I

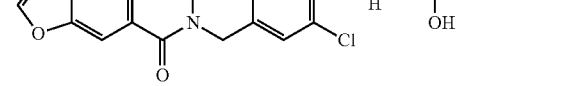

which comprises:
(i) reacting compound (IX) or a salt thereof;

Formula IX

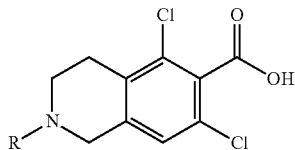

wherein, R is hydrogen or a N-protecting group,
with compound (X) or a salt thereof;

Formula X

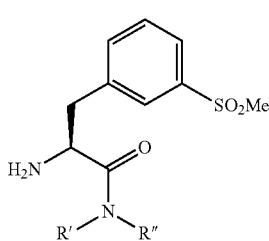

wherein, R' and R" independently selected from hydrogen, lower alkyl, alkyl, aryl or aralkyl (or) R' and R" taken together with the linking nitrogen atom to form a mono or bicyclic, heterocycle which may optionally contain in all ring moieties further nitrogen, oxygen or sulphur hetero atoms and which may optionally be substituted, to produce a compound (XI) or a salt thereof;

Formula XI (ii) optionally, deprotecting the N-protecting group 'R' to produce a compound (XIa) or a salt thereof;

Formula XIa (iii) reacting the compound obtained in the above step with benzofuran carboxylic acid (II) or its activated compound (XIII);

Formula II

Formula XIII wherein, R''' is acid activating group such as halogens, mesyl, tosyl, alkyl ester, alkyl carbamates etc., to produce compound (XII);

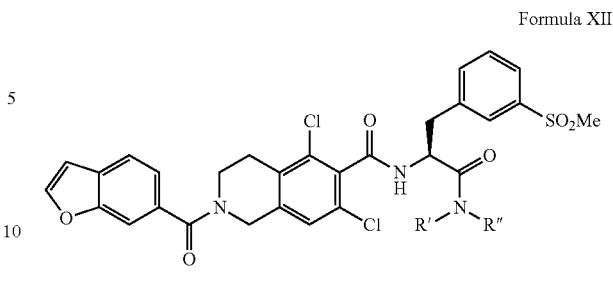

Formula XII (iv) hydrolyzing the compound (XII) to produce Lifitegrast (I).

Another embodiment of the present invention is to provide a process for the preparation of Lifitegrast (I), Formula I which comprises:
(i) hydogenolyzing the compound (IV) using a catalyst; and Formula IV (ii) isolating Lifitegrast (I).

BRIEF DESCRIPTION OF THE DRAWINGS

FIG. 1 Illustrates the X-ray powder diffraction pattern of dibenzylamine salt of Lifitegrast (XV) produced by the present invention.

FIG. 2 Illustrates the X-ray powder diffraction pattern of diphenylamine salt of Lifitegrast (XVI) produced by the present invention.

DETAILED DESCRIPTION OF THE INVENTION

An embodiment of the present invention is related to dibenzylamine salt of Lifitegrast (XV).

Another embodiment of the present invention provides the dibenzylamine salt of Lifitegrast (XV), which is characterized by XRD having 2θ peaks at 4.79, 5.79, 7.91, 9.59, 12.38, 15.25, 16.92, 18.05, 19.71, 20.92, 23.50, 25.62, 27.81 and 32.88±0.2 2θ.

Other embodiment of the present invention is related to a process for the purification of Lifitegrast (I). The process comprises, reacting Lifitegrast (I) with dibenzylamine in presence of solvent to produce Lifitegrast dibenzylamine salt (XV).

The Lifitegrast dibenzylamine salt (XV) is isolated as a solid or as such used in next step. The Lifitegrast dibenzylamine salt (XV) is reacted with an acid in presence or absence of a solvent to produce pure Lifitegrast (I).

The Lifitegrast (I) used in the above reaction is prepared by the process according to the present invention or by prior-art process.

Another embodiment of the present invention is related to diphenylamine salt of Lifitegrast (XVI).

Another embodiment of the present invention provides the diphenylamine salt of Lifitegrast (XVI), which is characterized by XRD having 2θ peaks at 5.03, 6.17, 7.33, 7.99, 8.56, 10.05, 12.39, 12.93, 15.90, 17.35, 18.08, 18.49, 18.88, 19.41, 19.69, 20.12, 20.29, 21.30, 21.72, 22.06, 22.77, 23.26, 23.63, 24.57, 25.47, 26.27, 26.77, 27.36, 28.25, 29.03, 30.82, 31.97 and 35.16±0.2 2θ.

Other embodiment of the present invention is related to a process for the purification of Lifitegrast (I). The process comprises, reacting Lifitegrast (I) with diphenylamine in presence of solvent to produce Lifitegrast diphenylamine salt (XVI).

The Lifitegrast diphenylamine salt (XVI) is isolated as a solid or as such used in next step. The Lifitegrast diphenylamine salt (XVI) is reacted with an acid in presence or absence of a solvent to produce pure Lifitegrast (I).

The Lifitegrast (I) used in the above reaction is prepared by the process according to the present invention or by prior-art process.

Another embodiment of the present invention is to provide a process for the preparation of compound (XIV) or salt thereof, by reacting compound (IX) or salt thereof with an alkyl halide.

The reaction is carried out in presence of a base. The reaction is carried out in presence/absence of a solvent.

Yet another embodiment of the present invention provides the use of compound (XIV) or salt thereof in the preparation of Lifitegrast (I).

Yet another embodiment of the present invention is related to a process for the preparation of Lifitegrast (I).

The process comprises, compound (IX) is reacted with a compound (X) to produce compound (XI).

In various embodiments of the present invention is directed to compounds of Formula (IX) wherein R is hydrogen or N-protecting group comprises tert-butyloxycarbonyl (BoC), acetyl (Ac), carbobenzyloxy (Cbz or Z) group, p-methoxybenzyl carbonyl (Moz or MeOZ) group, Allyl carbamate (Alloc) group, benzoyl (Bz), benzyl (Bn), carbamate, 2,2,2-trichloroethyl carbamate (Troc), p-methoxybenzyl (PMB), 3,4-dimethoxybenzyl (DMPM), p-methoxyphenyl (PMP), 2-trimethylsilylethyl carbamate (Teoc) and the like. R' & R" is independently selected from hydrogen, lower alkyl, alkyl, aryl or aralkyl (or) R' & R" taken together with the linking nitrogen atom to form a mono or bicyclic, heterocycle which may optionally contain in all ring moieties further nitrogen, oxygen or sulphur hetero atoms and which may optionally be substituted. Preferably, 4-phenyl-2-oxazolidinone, dicyclohexylamine and the like.

The reaction is carried out in the presence of a base and in the presence/absence of a solvent. The reaction is carried out in presence of a coupling agent.

The compound (XI) is isolated as a solid or as such used in next step. Optionally, the compound (XI) is subjected to purification either by column chromatography or by crystallization by dissolving in a solvent or by adding an anti-solvent.

In other embodiment of the present invention, the compound (XI) is optionally deprotected to produce compound (XIa) or salt thereof. The N-deprotetion of compound (XI) is carried out in presence of an acid, a base or a reducing agent. The reaction is carried out in the presence/absence of a solvent.

In another embodiment of the present invention, the compound (XIa) or salt thereof is reacted with benzofuran-6-carboxylic acid (II) or its active derivative (XIII) to produce compound (XII). The reaction is carried out in the presence of a base and in the presence/absence of a solvent. The reaction is carried out in presence of a coupling agent.

The compound (XII) is isolated as a solid or as such used in next step. Optionally, the compound (XII) is subjected to purification either by column chromatography or by crystallization by dissolving in a solvent or by adding an anti-solvent.

In another embodiment of the present invention, the activated compound (XIII) is produced by treating benzofuran-6-carboxylic acid (II) with activating group R'" to produce activated compound (XIII).

wherein, R'" is acid activating group such as halogens, mesyl, tosyl, alkyl ester, alkyl carbamates etc.

In another embodiment of the present invention, the compound (XII) is hydrolyzed to produce Lifitegrast. The reaction is carried out using a base or an acid. The reaction is carried out in absence or presence of a solvent.

Lifitegrast is isolated as a solid crystalline form. Optionally, Lifitegrast is subjected to purification either by column chromatography or by crystallization by dissolving in a solvent or by adding an anti-solvent.

In another embodiment of the present invention directed to a process for the preparation of Lifitegrast. The process comprises, hydrogenolyging compound (IV) using a catalyst. The reaction is carried out in presence of hydrogen gas.

The compound (IV) is prepared according to the present invention using appropriate intermediate compounds or by known methods.

In various embodiment of the present invention, the solvent comprises water, methanol, ethanol, propanol, isopropanol, butanol, isobutanol, toluene, benzene, o-xylene, m-xylene, p-xylene, acetone, methyl ethyl ketone, methyl isobutyl ketone, acetonitrile, ethyl acetate, methylene chloride, chloroform, dioxane, dimethylformamide, dimethyl sulfoxide, tetrahydrofuran, methyl tert-butyl ether, diethyl ether, hexane, cyclohexane, heptanes or mixture thereof.

In various embodiment of the present invention, the acid comprises hydrochloric acid, nitric acid, phosphoric acid, sulfuric acid, boric acid, hydrofluoric acid, hydrobromic acid, perchloric acid and hydroiodic acid, periodic acid and trichloroisocyanuric acid, trifluoro acetic acid or mixtures thereof.

In various embodiment of the present invention, the base comprises an organic base selected from triethylamine, pyridine, morpholine, methyl amine, diisopropyl ethyl amine, 1,8-Diazabicyclo[5.4.0]undec-7-ene (DBU), 1,4-di-azabicyclo[2.2.2]octane (DABCO) and 2,6-Lutidine or an inorganic base selected from potassium methoxide, potassium ethoxide, potassium tertiary butoxide, sodium methoxide, sodium ethoxide, sodium tertiary butoxide, sodium hydroxide, potassium hydroxide, lithium hydroxide, sodium carbonate, potassium carbonate, sodium bicarbonate, potassium bicarbonate, sodium acetate, potassium acetate; ammonia, ammonium cerium(IV) nitrate (CAN), sodium in liquid ammonia or sodium naphthalenide, samarium iodide, tributyltin hydride or mixtures thereof.

In various embodiment of the present invention, the coupling agent selected from O-benzotriazole-1-yl-1,1,3,3-tetramethyluronium tetrafluoroborate (TBTU), 1,3-dicyclohexylcarbodiimide (DCC), diisopropylcarbodiimide (DICwut), 2-(1H-benzotriazole-1-yl)-1,1,3,3-tetramethyluronium (HBTU), benzotriazole-1-yl-oxy-tris(dimethylamino)phosphonium (BOP), benzotriazole-1-yl-oxy-tris-(pyrrolidino)-phosphonum (PyBOP), bromo-tris-pyrrolidino-phosphoniumhexaflurophosphate (PyBrOP), tris(pyroolidino)-phosphonium hexaflurophosphate (py-COP), ethyl cyanoglyoxylate-2-oxime (Oxyma Pure), O-(6-chloro-1-hydrocibenzotriazol-1-yl)-1,1,3,3-tetramethyluronium tetrafluoroborate (TCTU), 2-ethoxycarbonyl-1,2-dihydropoquinoline (EEDQ), 2-(1H-7-azabenzotriazol-1-yl)-1,1,3,3-tetramethyl uronium hexafluorophosphate (HATU), 1-cyano-2-ethoxy-2-oxoethydenminooxy)dimethylamino-morpholion-carbenium hexafluorophosphate (COMU) performed active esters either individually or as a combination thereof.

The following example(s) illustrate the nature of the invention and are provided for illustrative purposes only and should not be construed to limit the scope of the invention.

EXAMPLES

Example 1: A Process for the Preparation of Lifitegrast

Stage-I A Process for the Preparation of Dichloro Quinoline Ester Compound (IXa)

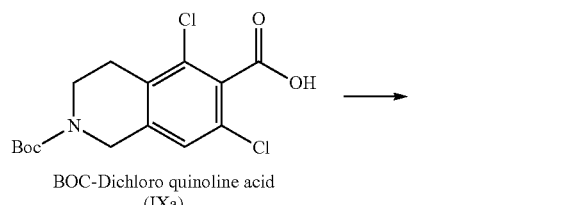

BOC-Dichloro quinoline acid
(IXa)

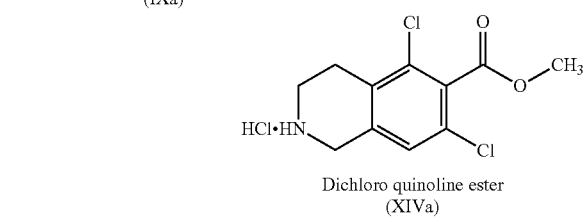

Dichloro quinoline ester
(XIVa)

A solution of BOC-Dichloro quinoline acid compound (20 g, 0.578 mmol) in dimethyl formamide (60 ml) was added with methyl iodide (9.84 g, 0.693 mmol). Sodium carbonate was added to the above reaction mixture (9.18 g, 0.867 mmol) and stirred at 25-35° C. for 2 hours. After completion of the reaction, the reaction mass was distilled under reduced pressure at below 70° C. The crude was dissolved in methylene chloride (100 ml) and washed with water (2×200 ml). The layers were separated. Hydrogen chloride in 1,4-dioxane was added (80 ml, Assay: ~15%) to the organic layer and stirred the mass for 2 h at 25-35° C. The product was filtered and washed with methylene chloride (40 ml). The compound was dried in vacuum oven at 60-65° C.

Stage-II: Preparation of Quinoline Methylate Compound (VIa)

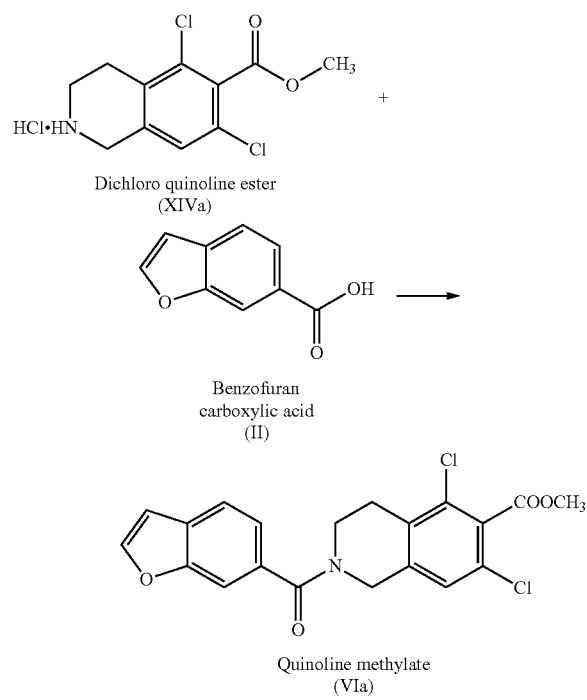

Quinoline methylate
(VIa)

A solution of benzofuran-6-carboxylic acid (7.75 g, 0.478 mmol) in tetrahydrofuran (67.5 ml) was added with triethylamine (23.03 g, 2.275 mmol) and 3-[bis(dimethylamino)methyliumyl]-3H-benzotriazol-1-oxide hexafluoro phosphate (HBTU, 18.98 g, 0.50 mmol) for 30 minutes at 25-35° C. Dichloro quinoline ester (13.5 g, 0.455 mmol) was added to the above reaction mixture at 25-35° C. and stirred at 25-35° C. for 3 hours. Water (162 ml) was added to the reaction mass at 25-35° C. and stirred the mass for 1 h at 25-35° C. The product was filtered and washed with water. The filter cake was washed with methanol. The compound was dried in vacuum oven at 60-65° C.

Stage-III: Preparation of Quinoline Acid Compound (VI)

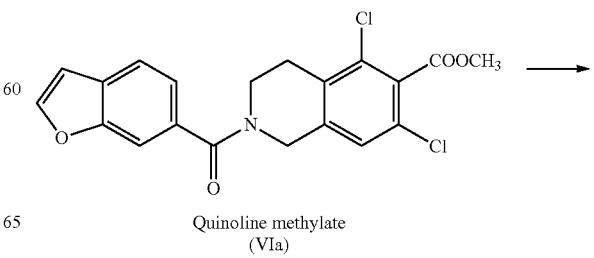

Quinoline methylate
(VIa)

-continued

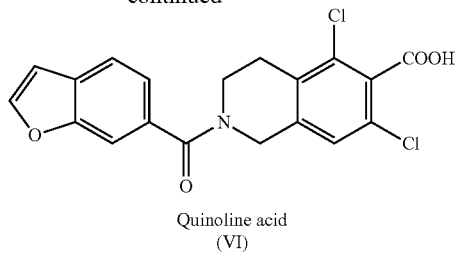

Quinoline acid
(VI)

A solution of quinoline methylate compound (14 g, 0.346 mmol) in pyridine (42 ml) was added with lithium iodide hydrate (23.18 g, 1.731 mmol) at 105-100° C. for 6-8 hours. After completion of the reaction, the reaction mass was cooled to 25-35° C. and water (70 ml) was added to the reaction mass. Hydrochloric acid (49 ml) was added at 10-20° C. to adjust the pH of the reaction mass to 2. Product was filtered and washed with water. Filter cake was washed with ethyl acetate. The compound was dried under vacuum at 60-65° C.

Stage-IV: Preparation of Lifitegrast Tech.

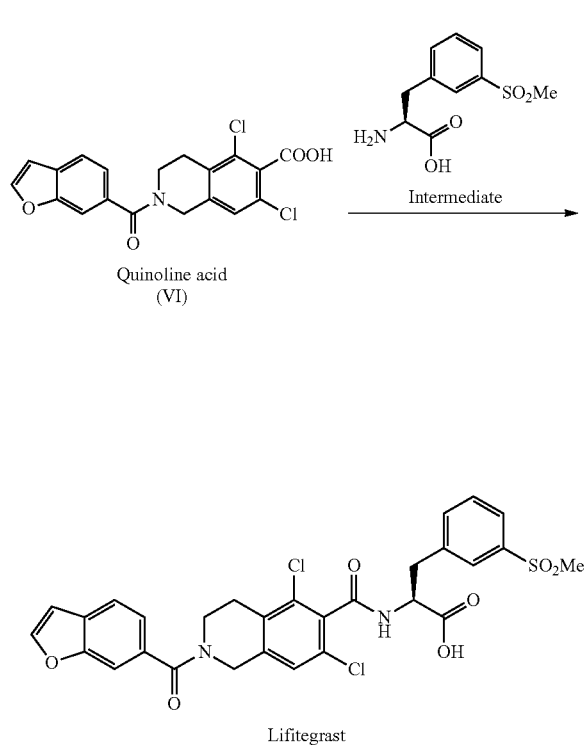

Quinoline acid
(VI)

Lifitegrast

A solution of quinoline acid compound (11 g, 0.281 mmol) in dimethyl formamide (110 ml) was added with triethylamine (14.26 g, 1.409 mmol) and HATU (11.79 g, 0.310 mmol) for 30 minutes at 25-35° C. HCl salt of the intermediate compound (8.7 g, 0.310 mmol) was added to the reaction mass at 25-35° C. and stirred at 25-35° C. for 2 hours. After completion of the reaction, MDC was added to the reaction mass. The reaction mass was washed with dilute hydrochloric acid (2×220 ml) followed by water (2×110 ml). Layers were separated. The organic was layer was distilled and the crude was isolated in ethanol. The compound was dried in vacuum oven at 60-65° C.

Example 2: A Process for the Preparation of Lifitegrast

Stage-I: Preparation of Compound of Formula (Xa)

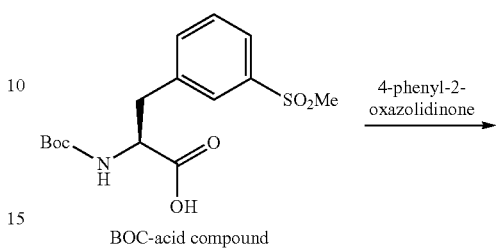

BOC-acid compound

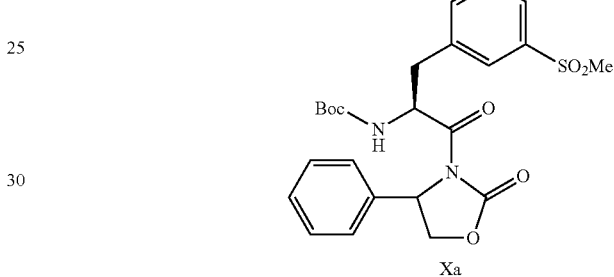

Xa

BOC-acid compound (25 g, 0.072 mmol) was added to diisopropyl ethyl amine (27.9 g, 0.216 mmol) and 3-[bis (dimethylamino)methyliumyl]-3H-benzotriazol-1-oxide hexaflorophosphate (HBTU, 27.6 g, 0.072 mmol) and stirred for 15 minutes at 25-35° C. in methylene chloride (125 ml, 5 volumes). 4-Phenyl-2-oxazolidinone (11.89 g, 0.072 mmol) was added to the reaction mass at 25-35° C. and stirred at 35-45° C. for 5 hours, after completion the reaction mass was washed with 5% sodium bicarbonate solution (125 ml) and washed with water (125 ml). The organic layer was distilled under vacuum at below 50° C. to get the crude. The obtained crude was stirred in methanol (100 ml) for 30 min at 25-35° C., the product was filtered and washed with methanol (25 ml). The compound was dried in vacuum oven at 50-55° C.

Stage-II: Preparation of Compound of Formula (Xb)

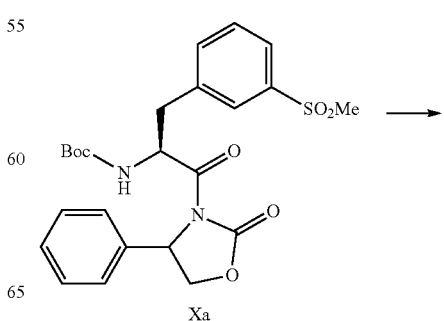

Xa

-continued

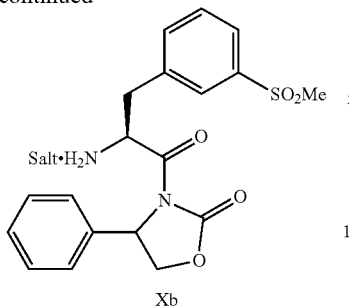

Xb

A solution of stage-I (23 g, 0.151 mmol) in methylene chloride (230 ml) was added to HCl in 1,4-dioxane (8M, 69 ml) at 25-35° C., stirred for 2 hours at 25-35° C. After completion, the reaction mass was filtered and washed with methylene dichloride (23 ml). The compound was dried under vacuum at 50-55° C. The reaction mass was filtered and washed with methylene dichloride (23 ml), then the compound was dried under vacuum at 50-55° C.

Stage-III: Preparation of Compound of Formula XX

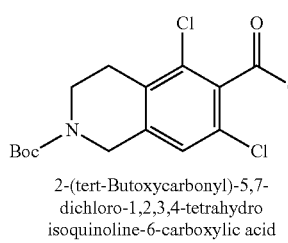

2-(tert-Butoxycarbonyl)-5,7-dichloro-1,2,3,4-tetrahydro isoquinoline-6-carboxylic acid

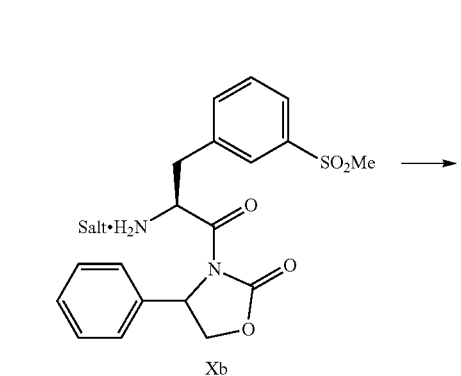

Xb

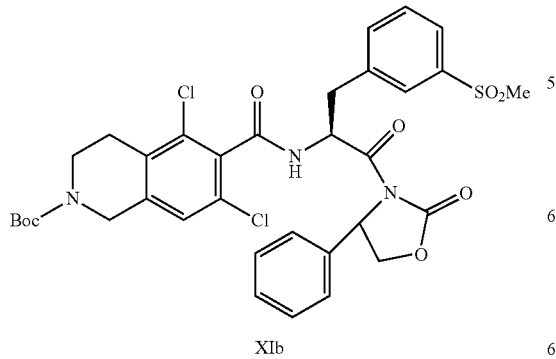

XIb 2-(tert-Butoxycarbonyl)-5,7-dichloro-1,2,3,4-tetrahydroisoquinoline-6-carboxylic acid (13 g, 0.037 mmol) was added to triethyl amine (11.4 g, 0.11 mmol) and 3-[bis(dimethylamino)methylium-yl]-3h-benzotriazol-1-oxide hexaflorophosphate (HBTU, 17.09 g, 0.04 mmol) and stirred for 15 minutes at 25-35° C. in dimethyl formamide (65 ml, 5 volumes) and then stage-II product (16 g, 0.037 mmol) was added to the reaction mass at 25-35° C. and stirred at 35-45° C. for 5 hours. After completion of the reaction, DMF was distilled under vacuum at below 60° C. The residue was dissolved in ethyl acetate and washed with about 5% sodium bicarbonate solution (65 ml) and followed by washed with water (65 ml). The organic layer was distilled under vacuum at below 50° C. to get the product. The obtained crude was stirred in hexane (30 ml) for 30 min at 25-35° C., the product was filtered and washed with hexane (10 ml). The compound was dried in vacuum oven at 50-55° C.

Stage-IV: Preparation of compound of formula XXI

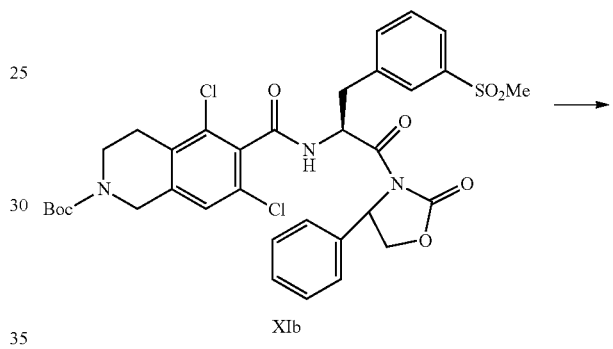

XIb

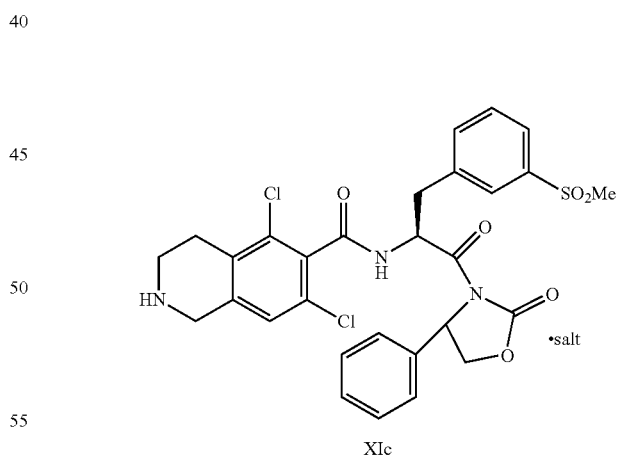

XIc

A solution of stage-III (18 g, 0.25 mmol) in methylene chloride (162 ml) was added to HCl in 1,4-dioxane (8M, 54 ml) at 25-35° C., stirred for 2-4 hours at 25-35° C. After completion of the reaction, the mass was distilled under vacuum at below 60° C., then methyl tert-butyl ether (MTBE, 90 ml) was added to the residue and stirred for 30 minutes at 25-35° C., the reaction mass was filtered and washed with MTBE (18 ml), the compound was dried under vacuum at 50-55° C.

Stage-V: Preparation of Compound of Formula XIIa

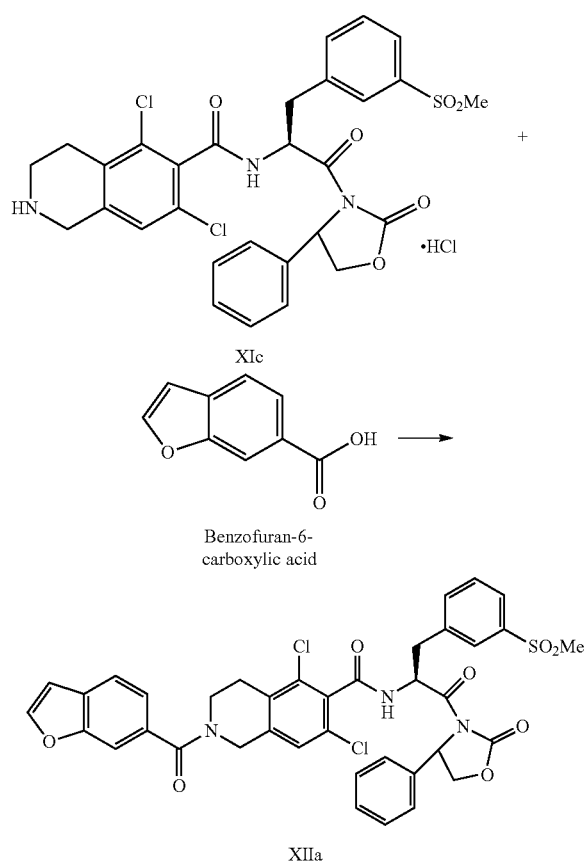

Benzofuran-6-carboxylic acid (4 g, 0.024 mmol) was added to triethyl amine (7.5 g, 0.72 mmol) and 3-[bis (dimethylamino) methylium-yl]-3H-benzotriazol-1-oxide hexaflorophosphate (HBTU, 11.2 g, 0.029 mmol), then stirred for 15 minutes at 25-35° C. in dimethyl formamide (40 ml, 10 volumes) and then stage-IV (16.1 g, 0.024 mmol) was added to the reaction mass at 25-35° C. and stirred at 35-45° C. for 5 hours. After completion of the reaction, DMF was distilled under vacuum at below 60° C. The residue was dissolved in ethyl acetate and washed with about 5% sodium bicarbonate solution (40 ml) and water (40 ml). The organic layer was distilled under vacuum at below 50° C. to get the product. The obtained crude was stirred in hexane (20 ml) for 30 min at 25-35° C., filtered the product and washed with hexane (10 ml). The compound was dried in vacuum oven at 50-55° C.

Stage-VI: Preparation of Lifitegrast

A solution of stage-V (10 g, 0.013 mmol) in a mixture of tetrahydrofuran and water (70 ml, 5:2) was treated with lithium hydroxide.H$_2$O (0.83 g, 0.019) at 25-35° C., stirred for 1-2 hours. After completion of the reaction, the mass was distilled under vacuum at below 50° C., the aqueous solution was extracted twice with ethyl acetate (50 ml) to remove the impurities. After that the aqueous solution was acidified to pH 2-3 with hydrochloric acid and extracted with ethyl acetate (50 ml). The organic layer was distilled under vacuum at below 50° C., the compound was dried under vacuum at 50-55° C.

Example 3: Purification of Lifitegrast (I)

Dibenzyl amine (1 mmol) was added to a suspension of Lifitegrast in methyl ethyl ketone (8 vol) at 60-65° C. and stirred for 15 min at 60-65° C. Reaction mass was allowed to cool to 25-35° C. and stirred for 30 min. The solid was filtered and washed with methyl ethyl ketone. The wet material was taken into water and basified with sodium hydroxide solution. The homogeneous solution was washed with mixture of ethyl acetate & toluene (2×5 vol). The aqueous layer was acidified with hydrochloric acid and stirred for 30 minutes and the solid was filtered and washed with methyl ethyl ketone. The compound was dried in oven at 60-65° C.

Example 4: Purification of Lifitegrast (I)

A solution of sodium hydroxide in water was added to a suspension of Lifitegrast in water and stirred for 15 min at 25-35° C. The clear solution was washed twice with ethyl acetate (organic solvents) and concentrated to get pure Lifitegrast salt. The salt was taken in to water and acidified with hydrochloric acid. The compound was extracted into ethyl acetate and concentrated to get pure Lifitegrast.

Example 5: Purification of Lifitegrast (I)

Diphenylamine (1 mmol) was added to a suspension of Lifitegrast in methyl ethyl ketone (8 vol) at 60-65° C. and stirred for 15 min at 60-65° C. Reaction mass was allowed to cool to 25-35° C. and stirred for 30 min. The solid was filtered and washed with methyl ethyl ketone. The wet material was taken into water and basified with sodium hydroxide solution. The homogeneous solution was washed with mixture of ethyl acetate & toluene (2×5 vol). The aqueous layer was acidified with hydrochloric acid and stirred for 30 minutes and the solid was filtered and washed with methyl ethyl ketone. The compound was dried in oven at 60-65° C.

Example 6: Purification of Lifitegrast (I)

A solution of tert-butyl amine was added to a suspension of Lifitegrast in acetone, stirred for 15 min at 25-35° C., filtered the solid and washed with acetone. The wet material was taken in to water and acidified with hydrochloric acid, stirred for 30 minutes and filtered the solid, then washed with mixture of methanol and water. The compound was dried in oven at 50-55° C.

We claim:
1. Dibenzylamine salt of Lifitegrast (XV)

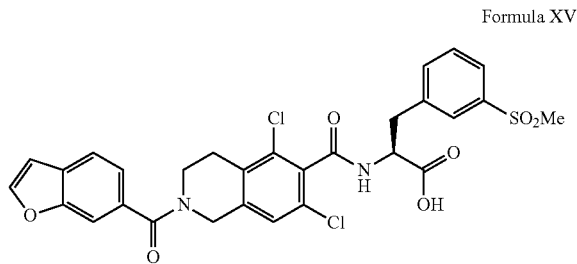

Formula XV

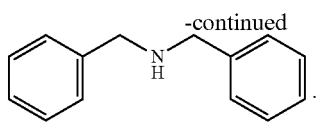

2. The dibenzylamine salt of Lifitegrast (XV) as claimed in claim 1, which is characterized by XRD having 2θ peaks at 4.79, 5.79, 7.91, 9.59, 12.38, 15.25, 16.92, 18.05, 19.71, 20.92, 23.50, 25.62, 27.81 and 32.88±0.2 2θ.

3. Diphenylamine salt of Lifitegrast (XVI)

Formula XVI

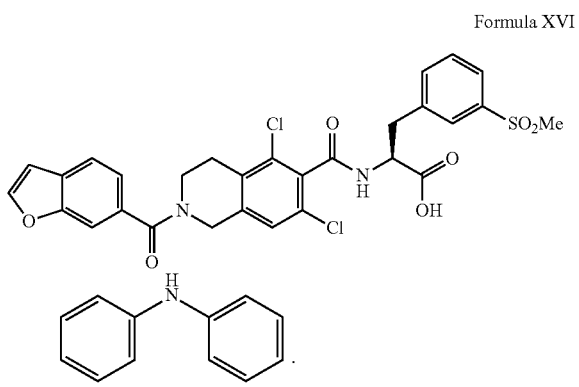

4. The diphenylamine salt of Lifitegrast (XVI) as claimed in claim 3, which is characterized by XRD having 2θ peaks at 5.03, 6.17, 7.33, 7.99, 8.56, 10.05, 12.39, 12.93, 15.90, 17.35, 18.08, 18.49, 18.88, 19.41, 19.69, 20.12, 20.29, 21.30, 21.72, 22.06, 22.77, 23.26, 23.63, 24.57, 25.47, 26.27, 26.77, 27.36, 28.25, 29.03, 30.82, 31.97 and 35.16±0.2 2θ.

5. A process for the purification of Lifitegrast (I) which comprises:
(i) treating Lifitegrast with dibenzylamine or diphenylamine in the presence of solvent selected from the group consisting of water, methanol, ethanol, propanol, isopropanol, butanol, isobutanol, toluene, benzene, o-xylene, m-xylene, p-xylene, acetone, methyl ethyl ketone, methyl isobutyl ketone, acetonitrile, ethyl acetate, methylene chloride, chloroform, dioxane, dimethylformamide, dimethyl sulfoxide, tetrahydrofuran, methyl tert-butyl ether, diethyl ether, hexane, cyclohexane, heptanes, and mixtures thereof, to get Lifitegrast dibenzylamine salt (XV) or Lifitegrast diphenylamine salt (XVI), respectively;
(ii) optionally, isolating the salt made in step (i);
(iii) treating the salt with an acid selected from the group consisting of hydrochloric acid, hydrobromic acid, sulfuric acid, phosphoric acid, methane sulfonic acid, para toluene sulfonic acid, and acetic acid in the presence or absence of said solvent, and
(iv) isolating pure Lifitegrast (I).

\* \* \* \* \*